United States Patent [19]

Griffin, Jr.

[11] 4,153,649

[45] May 8, 1979

[54] PHOSPHATE ESTER-TYPE REACTION PRODUCT AND METHOD OF PREPARING SAME

[75] Inventor: Thomas J. Griffin, Jr., Sand Springs, Okla.

[73] Assignee: The Dow Chemical Company, Midland, Mich.

[21] Appl. No.: 816,113

[22] Filed: Jul. 15, 1977

Related U.S. Application Data

[63] Continuation-in-part of Ser. No. 656,675, Feb. 9, 1976, abandoned, and Ser. No. 656,676, Feb. 9, 1976, abandoned.

[51] Int. Cl.$^2$ .......................... C07F 9/02; C07F 9/11
[52] U.S. Cl. ..................................... 260/950; 44/7 C;
252/8.55 D; 252/8.55 R; 252/316; 260/920; 260/978; 260/980

[58] Field of Search ................ 260/980, 950; 252/316, 252/8.55 R, 8.55 D; 44/7 C

[56] References Cited

U.S. PATENT DOCUMENTS

| | | |
|---|---|---|
| 3,020,303 | 2/1962 | Pianfetti et al. ................. 260/950 X |
| 3,133,787 | 5/1964 | Kelley, Jr. ......................... 260/925 X |
| 3,331,896 | 7/1967 | Eiseman, Jr. et al. ............... 260/980 |
| 3,494,949 | 2/1970 | Monroe et al. .................. 252/32.5 X |
| 3,755,509 | 8/1973 | Nunn, Jr. et al. ............... 260/950 X |
| 3,757,864 | 9/1973 | Crawford et al. .................. 166/308 |

*Primary Examiner*—Richard D. Lovering
*Attorney, Agent, or Firm*—G. H. Korfhage; Bruce M. Kanuch

[57] ABSTRACT

The reaction product of a hydroxy ether and a pentavalent phosphorus compound with a short chain and/or long chain alcohol can be employed to gel organic liquids by mixing the reaction product with an organic liquid in the presence of a multivalent metal cation.

56 Claims, No Drawings

PHOSPHATE ESTER-TYPE REACTION PRODUCT AND METHOD OF PREPARING SAME

CROSS-REFERENCE TO RELATED APPLICATIONS

This is a continuation-in-part application of two applications, Ser. Nos. 656,675 and 656,676, each filed Feb. 9, 1976, each now abandoned, and each entitled "Gelling of Organic Liquids".

BACKGROUND OF THE INVENTION

This invention relates to novel organic phosphoric acid esters and salts thereof. Such compounds result in improved high viscosity organic liquid based liquids, improved methods of thickening organic based liquids and improved methods of stimulating the flow of fluids through subterranean formations. Repesentative art relating to these types of compounds, their preparation and use are found in U.S. Pat. Nos. 2,245,649; 2,274,302; 2,329,707; 2,346,155; 2,885,417; 2,905,683; 2,983,678; 2,983,679; 3,010,903; 3,331,896; 3,470,222; 3,494,949; 3,505,374; 3,547,820; 3,575,859; 3,584,087; 3,706,822 and 3,757,864, the teachings of which are specifically incorporated herein by reference.

Other patents made of record in the parent applications include U.S. Pat. Nos. 1,944,530; 2,005,619; 3,020,303; 3,133,787; 3,484,474; 3,755,509; 3,757,864; and British Pat. No. 1,415,190, which is equivalent to Canadian Pat. No. 974,539.

Organic phosphoric acid esters have been employed in their free acid form and/or salts thereof as detergents, lubricating liquids, corrosion inhibitors, friction reducing agents, thickening agents and the like.

U.S. Pat. No. 3,757,864 teaches that certain aluminum salts of organic phosphoric acid esters are useful as friction reducing and gelling agents for nonpolar organic liquids. The salts are formed by reacting a basic aluminum compound with an ester which has been formed by reacting one or more monohydric aliphatic alcohols with a phosphorus compound such as $P_2O_5$, phosphorus oxychloride, $PCl_5$, $PF_5$, and the like.

It has now been discovered that certain metal salts of complex reaction products of a hydroxy ether and a phosphorus compound such as $P_2O_5$ are at least as effective as, and in many instances more effective than, the agents disclosed in U.S. Pat. No. 3,757,864 to gel refined oils and certain crude oils.

SUMMARY OF THE INVENTION

The product of the present invention is formed by reacting an essentially anhydrous hydroxy ether of the formula $ROR_1OH$ wherein R is a $C_1$ to $C_6$ alkyl group, $R_1$ is a $C_2$ or $C_3$ alkylene group and the total carbon atoms of $R_1$ and R range from 3 to about 8 with a pentavalent phosphorus compound which is substantially free from acid groups such as Cl, F and the like. When the total carbon atoms in the hydroxy ether is three or four, there is also reacted with the hydroxy ether and phosphorus compounds a long chain aliphatic monohydric alcohol containing at least five carbon atoms. A short chain aliphatic monohydric alcohol ($C_1$–$C_4$) can also be reacted therewith if desired. When the total carbon atoms in the hydroxy ether is five or more, there is reacted with the hydroxy ether and phosphorus compound either a long chain aliphatic alcohol (at least five carbons) or a short chain aliphatic monohydric alcohol ($C_1$–$C_4$) or a mixture thereof.

The above defined compounds are reacted with a pentavalent phosphorus compound for a period of time ranging from about 1.5 to about 6 hours at a temperature ranging from about 70° to about 90° C. to form the novel complex reaction product of the present invention. As more fully described hereinafter, reaction products having different selected characteristics can be prepared by reacting specific reactants and by varying the order in which they are reacted together.

To gel an organic liquid, or to reduce the friction pressure generated by an organic liquid flowing through a confining conduit, the reaction product is dispersed into an organic liquid along with a compound containing a multivalent cation capable of having a coordination number of 6, the reaction product and metal cation compound being employed in amounts and a specific ratio to each other to impart to the organic liquid a desired viscosity, or reduction in friction pressure, under substantially neutral conditions.

The gelled organic liquid can be employed as a fracturing fluid, as a carrying liquid for solids, and other utilities where organic liquids having a viscosity which is greater than the normal viscosity of the organic liquid is useful.

DETAILED DESCRIPTION OF THE INVENTION

The terms "short chain aliphatic monohydric alcohol" and "long chain aliphatic monohydric alcohol" as used herein, while differing from one another in length, each correspond to the formula (Aliph)OH, where each "Aliph" independently represents a substantially unsubstituted aliphatic hydrocarbon moiety. By "substantially" unsubstituted, it is intended to include within the alcohol term, compounds having a minor degree of substitution on the hydrocarbon chain wherein the solubility of the alcohol in nonpolar solvents is not significantly adversely affected, and wherein the nature of the substituent is such, e.g., a halogen, that the carbon chain is not interrupted by heterogenous atoms (e.g., N,O) and the predominate character of the compound is still that of a monohydric alcohol, i.e., so that the single hydroxyl group continues to be the predominate reactive group. Thus, the alcohol terms are not to be construed as embracing the hydroxy ether compounds employed as a separate component in the present invention. Preferably, however, "Aliph" represents a completely unsubstituted aliphatic hydrocarbon moiety, and where such meaning is hereinafter intended, the word "unsubstituted" is used, unmodified by the word "substantially".

The short chain aliphatic monohydric alcohol can be branched or straight chained, primary, secondary, or tertiary and may contain olefinic or acetylenic unsaturation but preferably is saturated. The preferred short chain alcohols are pimary, straight chained, unsubstituted, saturated alcohols. One or more can be employed. Specific alcohols which can be employed include, for example, methanol, ethanol, isopropyl alcohol, n-butyl alcohol, sec-butyl alcohol, tert-butyl alcohol and various mixtures thereof. Ethanol and methanol are preferred.

The long chain aliphatic monohydric alcohol can be saturated or olefinically or acetylenically unsaturated, branched or straight chained, and can be a primary, secondary, or tertiary alcohol. The alcohol contains at least 5 carbon atoms and preferably from 5 to about 12 carbon atoms. Examples of suitable alcohols include hexanol, decanol, oleyl alcohol, isooctyl alcohol, dodecanol, 4-decanol, triethylcarbinol, 3-ethyl-3-hexanol, 4-ethyl-3-hexanol and other similar alcohols. Mixtures of various alcohols are also suitable such as certain commercially available mixtures like, for example, AlFOL 810, AlFOL 610 and AlFOL 1012 from Continental Oil Company. The number indicates a mixture of alcohols containing from the lowest to highest number of carbon atoms. For example, AlFOL 810 is a mixture of saturated aliphatic alcohols containing $C_8$ and $C_{10}$ carbon atoms.

Suitable hydroxy ethers which can be employed include, for example, ethylene glycol monomethyl ether, ethylene glycol monoethyl ether, ethylene glycol mono-n-butyl ether, ethylene glycol mono-n-hexyl ether, ethylene glycol monoisobutyl ether, propylene glycol monoethyl ether, propylene glycol monoisobutyl ether, propylene glycol monomethyl ether, mixtures thereof and other like compounds.

The pentavalent phosphorus compound includes, for example, $P_2O_5$ and the like. $P_2O_5$ is preferred. A portion of the $P_2O_5$ may be replaced with a polyphosphoric acid solution; however, in the latter case polyphosphoric acid solutions containing an equivalent of at least about 83 percent by weight $P_2O_5$ are preferred. A maximum substitution of up to about 15 percent, preferably only up to about 10 percent by weight, of the $P_2O_5$ is possible since it is preferred that the reaction be conducted under essentially anhydrous conditions.

The order of addition of the reactants has not been found critical. One method comprises mixing the alcohols and hydroxy ether together and then slowly adding the phosphorus compound thereto with cooling of the reaction mixture to maintain the temperature below about 70° C. After complete addition of the phosphorus compound the temperature of the reaction mixture is maintained at between 70° and 90° C., preferably 80° to 90° C., for from about 1.5 to about 6, preferably from about 1.5 to about 3 hours, but in any event for a sufficient time for the reaction to go to the desired degree of completion. These temperatures are for a reaction conducted at atmospheric pressures. The reaction mixture can be employed as is or as a concentrate in an organic liquid or freeze point depressant, such as an aromatic hydrocarbon or the like.

It has also be discovered that in certain cases when one of the reactants is a short chain alcohol, e.g., methanol or ethanol, reaction products having superior gelling properties can be prepared by adding the phosphorus compound to only a hydroxy ether, and if employed a long chain alcohol followed by a short reaction period of from about 5 to 30 minutes at a reaction temperature of from about 70° to 90° C., then cooling the reaction mixture to below about 70° C., preferably to about 50° C., and then adding the short chain alcohol and continuing the reaction until completion at a temperature of from about 70° to about 90° C., preferably from about 80° to about 90° C.

Where only the hydroxy ether and a short chain alcohol are employed as reactants it is especially preferred to first react the hydroxy ether with the phosphorus compound and then add the short chain alcohol. The separate addition technique is also most preferred when the short chain alcohol is methanol.

The reactants should be reacted together in certain molar ratios to provide reaction products having the most favorable gelling characteristics. The molar ratios which are operable are set forth in the following table wherein $P_2O_5$ is the pentavalent phosphorus compound. Where a mixture of $P_2O_5$ and polyphosphoric acid is employed, the ratios set forth below are based on the total of the moles of $P_2O_5$ provided by the $P_2O_5$ component plus the equivalent moles of $P_2O_5$ provided by the polyphosphoric acid component.

| Mole Ratio to total $P_2O_5$ (or $P_2O_5$ equivalent) | Reactants | | |
|---|---|---|---|
| | Short Chain Alcohol | $ROR_1OH$ | Long Chain Alcohol |
| Operable | 0 to 5.0 | 0.4 to 4.5 | 0 to 4.0 |
| Preferred | 0.9 to 2.0 | 0.8 to 1.8 | 0 to 1.4 |

The mole ratio of the total of the short chain and/or long chain alcohol and the hydroxy ether to total phosphorus pentoxide ranges from about 2.8:1 to about 7.0:1 with the most preferred ratio being about 3.64:1.

The reaction product is a complex mixture of phosphate esters the exact identity of which has not been determined. It has, however, been found that reaction products produced in an essentially identical manner will have essentially identical gelling properties.

Organic liquids which can be gelled with the product of the present invention are generally nonpolar and include, for example, aliphatic hydrocarbons and halogenated, e.g., chlorinated, hydrocarbons, and mixtures thereof. Preferred aliphatic hydrocarbons include refined paraffinic oils, such as lubricating oils, kerosene, diesel oil, fuel oil and the like. Certain aromatic compounds, e.g., xylene, are also suitable, as are certain crude oils. The effectiveness and optimum quantities of reaction product to increase the viscosity of any particular organic liquid should be ascertained prior to a large scale use. Since crude oils vary almost infinitely in composition, small scale tests are particularly advisable when crude oil is to be employed. Of the crude oils, those having an API gravity of above about 25 are generally preferred, i.e., the lighter crude oils.

To gel an organic liquid, the reaction product is mixed with the organic liquid along with, preferably, a basic compound containing a multivalent metal cation capable of having a coordination number of 6. By basic it is meant that an aqueous solution of the compound has a pH greater than 7. Alternatively, neutral and acidic salts capable of providing such a metal cation may be used in combination with sufficient base, such as an alkali metal hydroxide or an alkali metal or ammonium salt of an ethylenepolyaminepolycarboxylic acid, to neutralize the acidity of the ester reaction product (and any other acidic species in the medium).

Suitable compounds containing a multivalent metal cation which can be employed with a separate source of base include ferric nitrate, aluminum nitrate, and rare earth metal salts of the elements of atomic numbers 57–71. Preferred are basic aluminum salts such as aluminum isopropoxide (also known as aluminum isopropylate) or an alkali metal aluminate. Other basic aluminum compounds such as hydrated alumina may also be employed. Thus, one property by which the reaction product of the present invention is characterizable is its ability to gel kerosene when admixed therewith with an effective amount of sodium aluminate, though of course embodiments of the reaction product possessing that specific property have other utilities as well.

The reaction product and metal compound are employed in a total amount and weight ratio to each other to produce a gelled product having a desired viscosity. These amounts and ratios will vary and are dependent on the reactants which are employed to make the reaction product, the exact metal compound, the organic liquid employed, and the desired viscosity. The examples of the invention which follow provide specific embodiments of suitable ranges. However, the invention is not limited thereto since it is within the skill of the art to make these determinations for specific reaction products, metal salts and organic liquids. For example, when about 8 gallons of the phosphate ester are employed per 1000 gallons of organic liquid from about 0.5 to about 2.5 gallons of a 38 percent by weight of a sodium aluminate solution per 1000 gallons of organic liquid is suitable. For different quantities of phosphate ester the amount of metal salt will vary proportionally.

When the reaction product is employed to increase the viscosity of an organic liquid which is to be employed as a fracturing fluid standard techniques of mixing and fracturing can be employed. For example, a suitable amount of a reaction product which has been previously prepared is mixed with, for example, kerosene or crude oil in a mixing tank along with a suitable metal compound under basic conditions. The so prepared fluid is then employed to fracture, for example, a petroleum producing formation employing standard equipment and techniques known in the art. In general, the method comprises pumping the so prepared fluid through a borehole and into contact with the subterranean formation to be fractured at a sufficient pressure to fracture the same. For fracturing techniques the fluid should have a viscosity ranging from about 10 to 500 centipoise measured with a Fann viscometer at 160 sec$^{-1}$ and 30° C. A sufficient amount of the reaction product and multivalent metal activator are employed to bring the viscosity of the organic liquid to a value within this range. Generally from about 1 to 25 gallons of reaction product per 1000 gallons of organic liquid is suitable.

The results of various tests are set forth in the following tables. Various reaction products were prepared and their ability to gel kerosene and/or crude oil was determined. The procedures employed to prepare the reaction product and the gel in the following series of tests are as follows:

Preparation of Alkyl Phosphates by Mixed Addition

The desired quantities of alcohol and hydroxy ether were placed in a reaction flask equipped with a mechanical stirrer, reflux condenser, thermometer and heating mantle. With continuous stirring, P$_2$O$_5$ was added, maintaining the temperatures below 70° C. with cooling. After complete addition of P$_2$O$_5$, the mixture was heated to 80° C. and maintained for six hours. The product was then cooled, formulated as described hereinafter and checked for gelling in kerosene as set forth hereinafter.

Preparation of Alkyl Phosphates by Separate Addition

The procedure described directly hereinbefore was followed, except that the P$_2$O$_5$ was first added to the hydroxy ether, and if employed, a long-chain alcohol. After complete addition of the P$_2$O$_5$ and 15 minutes of mixing, the short-chain alcohol (methanol and/or ethanol) was added while the temperature of the reaction mixture was maintained below 50° C. by controlled addition. The mixture was then heated to 80° C. and reacted for six hours. The product was then cooled, formulated as described hereinafter and checked for gelling in kerosene in the manner described hereinafter.

Preparation of Alkyl Phosphate Esters Employing Polyphosphorous Acid

The first procedure described above was followed except that after two hours at 80° C., the mixture was cooled to 50° C. and a certain amount of polyphosphoric acid was added. The mixture was then heated to 80° C. for an additional 3½ hours.

Formulation of Gelling Agent

For ease of comparison, the products of the procedures described above were formulated into a premix by mixing 40.0 ml (77.3% by volume) of the ester reaction product with 11.7 ml (22.7% by volume) of an aromatic hydrocarbon solvent comprised primarily of a complex mixture of aromatics comprised of alkyl substituted benzenes and some alkyl substituted naphthalenes. The specifications of the aromatic solvent employed are: 18° API gravity; 90% minimum aromatics; 96% typical aromatics; 214° C. initial boiling point; 334° C. final boiling point.

Gelling Kerosene with Formulated Phosphate Esters

Four hundred milliliters of kerosene were placed in a one-quart Waring Blendor cup. While mixing at moderate speed, 3.2 ml (equivalent to 8 gal/1000 gal) of the formulated ester was added followed by dropwise addition of 0.45 ml of sodium aluminate (38% by weight active aqueous solution). The sample was then mixed for two minutes and the viscosity was determined using a Model 35 Fann viscometer with a number one rotor and bob and a medium spring at room temperature. Dial readings were recorded at all speeds initially, after one hour, after 3 or 5 hours and, if deemed necessary, after 24 hours. This process was then repeated using 0.50 and 0.55 ml of sodium aluminate. Based on these tests, additional tests were run to determine the amount of sodium aluminate giving the highest stable, apparent viscosity at 160 sec$^{-1}$ (100 RPM). This amount is set forth in Table I as percent by volume of the entire mixture. By stable viscosity is meant one which doesn't change appreciably after the first hour. In the Tables where a time is not indicated by the viscosity shown, the viscosity is the stable viscosity taken after 1 hour.

Gelling Crude Oil with Formulated Phosphate Esters

Crude oil gelling tests were conducted in the same manner as described above for gelling kerosene except that larger amounts of formulated ester and sodium aluminate were used.

TEST SERIES I

The following Table I sets forth the results of various tests of reaction products and the ability of certain phosphate esters to gel kerosene. Some of the reaction products come within the scope of the claimed invention while others are shown for comparative purposes. In the column identified as Short Chain Alcohol either ethanol or methanol was employed unless otherwise specifically noted in the column, e.g., in Test No. 29 isobutyl alcohol was employed as well as methanol. In the column identified as percent by vol. of sodium aluminate solution a range of percents indicates that the same viscosity of gelled fluid was obtained through the range indicated. In some tests this demonstrated little or no gelation was observed although a broad range was tested.

In Tables I and II, the abbreviations mean

EtOH - ethanol
MeOH - methanol
Mixed - The first procedure described for making the reaction product
Separate - The second procedure described for making the reaction product
EM - ethylene glycol monomethyl ether
EE - ethylene glycol monoethyl ether
EB - ethylene glycol mono-n-butyl ether
EH - ethylene glycol mono-n-hexyl ether
DB - diethylene glycol butyl ether
DM - diethylene glycol monomethyl ether
DE - diethylene glycol
IC3 - isopropyl alcohol
BE - butylene glycol ethyl ether
PM - propylene glycol monomethyl ether
810 - commercial mixture of $C_8$-$C_{10}$ alcohols - AlFOL 810
1012 - commercial mixture of $C_{10}$-$C_{12}$ alcohols - AlFOL 1012
IC4 - isobutyl alcohol
NC4 - normal butyl alcohol
610 - commercial mixture of $C_6$-$C_{10}$ alcohols - AlFOL 610
$C_{10}$-$C_{12}$ w/5 moles EO -adduct of a mixture of $C_{10}$-$C_{12}$ alcohols with 5 moles of ethylene oxide
$C_{12}$-$C_{15}$ w/3 moles EO - adduct of a mixture of $C_{12}$-$C_{15}$ alcohols with 3 moles of ethylene oxide

TABLE I

| Test No. | Percent by Vol. of Sodium Aluminate Solution | OH $R_1OR$ | Mole Ratio (Based on $P_2O_5=1$) Long Chain Alcohol | Short Chain Alcohol EtOH | Short Chain Alcohol MeOH | Procedure | Kerosene Viscosity at 1 Hour Unless Otherwise Noted (cps at 160 sec) |
|---|---|---|---|---|---|---|---|
| 1 | .11 | EM(1.82) | 810(1.82) | — | — | Mixed | 120-162 (range because of difficult reading) |
| 2 | .11 | EM(0.91) | 810(1.82) | — | 0.91 | Separate | 159-180 |
| 3 | .13 | EM(1.82) | 810(0.91) | — | 0.91 | Separate | 1 hr - 100  24 hrs - 255 |
| 4 | .15 | EM(0.91) | 810(0.91) | — | 1.82 | Separate | 258 |
| 5 | .1-.13 | EM(1.82) | — | — | 1.82 | Separate | Insoluble |
| 6 | .15 | EE(0.91) | 810(0.91) | — | 1.82 | Separate | 1 hr - 279  3 hrs - 315 |
| 7 | .1-.13 | EE(1.82) | — | — | 1.82 | Separate | Insoluble |
| 8 | .1 | EB(1.82) | 810(1.82) | — | — | Mixed | 75 |
| 9 | .09 | EB(0.91) | 810(1.82) | — | 0.91 | Separate | 105 |
| 10 | .13 | EB(0.46) | 810(1.36) | — | 1.82 | Separate | 190 |
| 11 | .11 | EB(0.46) | 810(0.91) | — | 1.82 | Mixed | 159 |
| 12 | .13 | EB(0.91) | 810(0.91) | — | 1.82 | Separate | 267 |
| 13 | .12 | EB(0.91) | 810(0.91) | 1.82 | — | Mixed | 180-201 |
| 14 | .11-.13 | EB(0.91) | 1012(0.91) | — | 1.82 | Separate | 177-180 |
| 15 | .13 | EB(0.91) | 1012(0.91) | 1.82 | — | Mixed | 126 |
| 16 | .11 | EB(0.91) | 810(0.91) | 1.82 | — | Separate | 201 |
| 17 | .11 | EB(1.82) | 810(0.91) | — | 0.91 | Separate | 159 |
| 18 | .15 | EB(1.36) | 810(0.46) | — | 1.82 | Separate | 220 |
| 19 | .14-.15 | EB(1.82) | — | — | 1.82 | Separate | 1 hr - 144  24 hrs - 240 |
| 20 | .1 | EB(1.82) | — | — | 1.82 | Mixed | 30 |
| 21 | .18 | EB(1.82) | — | 1.82 | — | Separate | 111 |
| 22 | .12 | EH(0.91) | 810(0.91) | — | 1.82 | Separate | 147 |
| 23 | .13 | EH(1.82) | — | — | 1.82 | Separate | 150 |
| 24 | .1-.13 | DM(1.82) | 810(0.91) | — | 0.91 | Separate | 15 |
| 25 | .11 | DB(1.82) | — | — | 1.82 | Separate | 18 |
| 26 | .13 | PM(0.91) | 810(0.91) | — | 1.82 | Separate | 170 |
| 27 | .08-.18 | EB(1.82) | — | 1.82 | — | Mixed | No gel |
| 28 | .13 | EH(1.82) | — | — | 1.82 | Separate | 131-159 |
| 29 | .08-.18 | EB(0.91) | — | IC4(0.91) | 1.82 | Mixed | No gel |
| 30 | .08-.18 | EB(0.91) | — | 1.82 | NC4(0.91) | Mixed | No gel |
| 31 | .08-.18 | EB(0.91) | — | IC4(0.91) | 1.82 | Separate | No gel |
| 32 | .08-.18 | EB(0.91) | — | NC4(0.91) | 1.82 | Separate | No gel |
| 33 | .08-.18 | EB(3.64) | — | — | — | Mixed | No gel |
| 34 | .08-.18 | EE(1.82) | — | — | 1.82 | Separate | No gel |
| 35 | .13 | DE(0.46) | 810(0.91) | — | 1.82 | Mixed | 72 |
| 36 | .08-.18 | DE(0.91) | 810(0.91) | — | 1.82 | Mixed | No gel |
| 37 | .11 | 2,2,4,4-tetra methylcyclo butanediol (0.46) | 810(0.91) | — | 1.82 | Separate | 50 |
| 38 | .12 | — | 1012(1.32) | 1.32 | 1.0 | Mixed | 168 |
| 39 | .08-.18 | — | $C_{10}$-$C_{12}$ w/5 moles EO(1.82) | — | 1.82 | Separate | No gel |
| 40 | .08-.18 | — | $C_{12}$-$C_{15}$ w/3 moles EO(1.82) | — | 1.82 | Separate | No gel |
| 41 | .13 | — | Adduct Hexanol + 4 moles EO | — | — | Mixed | 24 |

TABLE I-continued

| Test No. | Percent by Vol. of Sodium Aluminate Solution | OH R₁OR | Mole Ratio (Based on $P_2O_5$=1) Long Chain Alcohol | Short Chain Alcohol EtOH | MeOH | Procedure | Kerosene Viscosity at 1 Hour Unless Otherwise Noted (cps at 160 sec) |
|---|---|---|---|---|---|---|---|
| | | | 70%+30% isopropanol (1.82) + 810(1.82) | | | | |
| 42 | .12 | — | 810(1.82) | — | 1.82 | Mixed | 135 |
| 43 | .11 | — | 810(1.82) | — | 1.82 | Separate | 160–180 |
| 44 | .13 | — | 610(1.82) | 1.82 | — | Mixed | 168 |
| 45 | .13 | — | 810(1.82) | 1.82 | — | Mixed | 162 |
| 46 | .11 | — | 810(1.82) | 1.82 | — | Separate | 165 |
| 47 | .14–.15 | — | 610(1.32) | 1.32 | 1.00 | Mixed | 195 |
| 48 | .11 | — | 810(1.82) | — | 1.82 | Separate | 180 |
| 49 | .11 | — | 810(1.82) | — | 2.61 | Separate | 165 |
| 50 | .12 | — | 810(1.70) | — | 1.70 | Separate | 210 |
| 51 | .13 | — | 1,4 butanediol (0.46) 810(0.91) | — | 1.82 | Separate | 87 |
| 52 | .08–.18 | — | 1,4 butanediol (0.91) 810(0.91) | — | 1.82 | Separate | No gel |
| 53 | .13 | — | diethylene glycol (0.46) 810(0.91) | — | 1.82 | Separate | 72 |
| 54 | .12 | EB(1.21) | 810(0.91) | — | 1.82 | Separate | 200 |
| 55 | .113 | EB(0.91) | 810(0.91) | NC4(1.82) | — | Mixed | 123 |
| 56 | .125 | EB(0.91) | 810(0.91) | IC4(1.82) | — | Mixed | 78 |
| 57 | .125–.138 | EB(0.63) | 2 methylcyclohexanol (0.91) | — | 1.82 | Separate | No gel |
| 58 | .113 | EB(1.13) | 810(1.13) | — | 2.25 | Separate | 204 |
| 59 | .125–.138 | EB(0.63) | 810(0.63) | — | 1.25 | Separate | No gel |
| 60 | .125 | EB(0.91) | Oleyl Alcohol(0.91) | — | 1.82 | Separate | 63 |
| 61 | .138 | EB(0.75) | 810(0.75) | — | 1.5 | Separate | 129 |
| 62 | .094 | Eb(1.5) | 810(1.5) | — | 3.0 | Separate | 114 |
| 63 | .125 | EB(0.91) | 810(0.91)IC3(1.82) | — | Separate | | 57 |
| 64 | .075 | EB(1.75) | 810(1.75) | — | 3.50 | Separate | 51 |
| 65 | 0–.75 | BE(0.91) | 810(0.91) | — | 1.82 | Separate | No gel |

TEST SERIES II room temperature. The results of the tests are set forth in the following Table II.

TABLE II

| Test No. | ROR₁OH | Mole Ratio Based on 1 Mole $P_2O_5$ Long Chain Alcohol | Short Chain Alcohol EtOH | MeOH | Viscosity Kerosene | Crude | |
|---|---|---|---|---|---|---|---|
| 1 | — | 810(1.82) | 1.82 | — | 150 | 129 | |
| 2 | — | 610(1.82) | 1.82 | — | 168 | 123 | |
| 3 | — | 1012(1.82) | 1.32 | 1.0 | 168 | 63 | |
| 4 | — | 610(1.32) | 1.32 | 1.0 | 195 | 105 | |
| 5 | EB(0.91) | 810(0.91) | 1.82 | — | 180 | 99 | |
| 6 | EB(1.82) | — | — | 1.82 | 144 | 6 | (precipitate) |
| 7 | DB(1.82) | — | — | 1.82 | 18 | 6 | (precipitate) |
| 8 | EB(1.82) | 810(1.82) | — | — | 75 | 6 | |
| 9 | EM(1.82) | 810(0.91) | — | 0.91 | 100 | 18 | (precipitate) |
| 10 | EB(0.91) | 810(0.91) | — | 1.82 | 267 | 147 | |
| 11 | EE(0.91) | 810(0.91) | — | 1.82 | 279 | 144 | |
| 12 | EM(0.91) | 810(0.91) | — | 1.82 | 258 | 87 | |
| 13 | EH(0.91) | 810(0.91) | — | 1.82 | 147 | 132 | |
| 14 | — | 810(1.82) | — | 1.82 | 180 | 96 | |
| 15 | EB(0.91) | 810(1.82) | — | 0.91 | 105 | 42 | |
| 16 | EM(0.91) | 810(1.82) | — | 0.91 | 180 | 99 | |
| 17 | DE(0.46) | 810(0.91) | — | 1.82 | 72 | 6 | (precipitate) |
| 18 | — | 810(1.82) | — | 2.62 | 165 | 105 | |

Various reaction products were employed to gel both kerosene and a crude oil. The products were all prepared by the same procedures set forth in the previous series of tests. To gel the kerosene an equivalent of 8 gallons of the reaction product formulation was mixed per 1000 gallons of kerosene. An equivalent of 0.08–1.8 gallons per 1000 gallons of kerosene of a 38 percent by weight aqueous solution of sodium aluminate was employed to activate the gel. For the crude oil, an equivalent of 20 gallons and 2.0–4.5 gallons of the reaction product and sodium aluminate, respectively, were employed. The viscosity was measured at 160 sec$^{-1}$ at

TEST SERIES III

In this series of tests a certain 15 percent by weight polyphosphoric acid was substituted for $P_2O_5$. The reactants comprised 0.91 mole of 810, 0.91 mole EB, 1.82 moles MeOH and 1 mole $P_2O_5$ (for polyphosphoric acid calculated on a $P_2O_5$ basis). The procedure employed to prepare the reaction product was the same as the mixed procedure set forth for the first series of tests except that after the original mixture had been maintained at 80° C. for two hours the mixture was cooled to 50° C., and polyphosphoric acid was added. The mixture was then maintained at 80° C. for an additional 3.5 hours. The reaction product was cooled and formulated with 22.7 percent by volume of an aromatic hydrocarbon solvent and then employed to gel kerosene in the manner as described hereinbefore. The results of these tests were a viscosity of 267 cps without polyphosphoric acid substitution and 150 cps with a substitution of polyphosphoric acid for 15% by weight of the $P_2O_5$. The polyphosphoric acid was a commercially available technical grade composition composed of ortho and polymeric acids. The composition contained a minimum of 83 percent by weight $P_2O_5$ and a maximum of 86 percent with an equivalent phosphoric acid ($H_3PO_4$) of 114.6 percent and 118.7 percent, respectively.

TEST SERIES IV

The reaction conditions (temperature and time) were varied to prepare the reaction product investigated in this series of tests. The reactants were the same as employed in the immediately proceeding series of tests except 100 percent of $P_2O_5$ was employed in all the tests. The separate procedure of reacting the ingredients was employed. The reaction products were employed to gel kerosene. The results are set forth in the following Table III.

TABLE III

| Test No. | Reaction Conditions | | Viscosity cps at 160 sec$^{-1}$ |
|---|---|---|---|
| | Temp. °C. | Time (Hrs). | |
| 1 | 90 | 1.5 | 225 |
| 2 | 90 | 3 | 230–250 |
| 3 | 80 | 3 | 230–225 |
| 4 | 80 | 6 | 230 |
| 5 | 70 | 6 | 240 |
| 6 | 60 | 6 | 200–210 |

TEST SERIES V

An alkyl phosphate was prepared by the separate addition technique by reacting 0.91 mole of 810 (Al-FOL810) with 0.91 mole of ethylene glycol mono-n-butyl ether and 1.82 moles of methanol. Employing the procedure set forth previously under the heading "Gelling Kerosene with Formulated Phosphate Esters" an attempt was made to gel various organic liquids. The results of these tests are set forth in the following Table IV.

TABLE IV

| Test No. | Organic Liquid | Viscosity (160 sec$^{-1}$) | Volume Percent of 38% Sodium Aluminate |
|---|---|---|---|
| 1 | CCL$_4$ | 48 | .088 |
| 2 | Octene-1 | 141 | .050 |
| 3 | N-undecane | 240 | .063 |

The phosphate ester would not gel certain aromatic hydrocarbons, e.g., benzene. In other tests, however, the phosphate ester did gel xylene, although the viscosity was difficult to measure because the gelled xylene exhibited the Weissenberg effect, i.e., it tended to climb the viscometer spindle.

TEST SERIES VI

A phosphate ester was prepared in the manner set forth in series V. Employing substantially the same procedure as set forth under the heading "Gelling Kerosene with Formulated Phosphate Esters", kerosene was successfully gelled using ferric nitrate and sodium ethylenediaminetetraacetic acid in lieu of sodium aluminate as the source of multivalent metal cation.

What is claimed is:

1. An organic phosphate ester composition having as a property the ability to increase the viscosity of kerosene when admixed in kerosene with sodium aluminate, said composition being prepared by the process which comprises the reaction of:
   A. a pentavalent phosphorus compound selected from the group consisting of $P_2O_5$ and a mixture of $P_2O_5$ with polyphosphoric acid;
   B. a hydroxy ether of the formula $ROR_1OH$ wherein R is a $C_1$ to $C_6$ alkyl group, $R_1$ is a $C_2$ or $C_3$ alkylene group and the total carbon atoms of R and $R_1$ range from 3 to about 8; and
   C. when the total carbon atoms of R and $R_1$ and is 3 or 4, a long chain substantially unsubstituted monohydric aliphatic alcohol containing at least 5 carbon atoms, but when the total carbon atoms of R and $R_1$ is 5 to 8, an alcohol selected from the group consisting of a long chain substantially unsubstituted monohydric aliphatic alcohol containing at least 5 carbon atoms, a short chain substantially unsubstituted monohydric aliphatic alcohol containing from 1 to 4 carbon atoms and a mixture of said alcohols, the individual mole ratios of the hydroxy ether, the long chain alcohol and the short chain alcohol to total $P_2O_5$ being within the ranges of 0.4:1 to 4.5:1; 0:1 to 4.0:1 and 0:1 to 5.0:1 respectively, said reaction being conducted at temperature ranging from about 70° to about 90° C. for a period of time of from about 1.5 to about 6 hours, and said pentavalent phosphorus compound, hydroxy ether, and alcohol or alcohols being provided in molar ratios and admixed in a sequence effective to provide a reaction product suitable for use in increasing the viscosity of kerosene.

2. The reaction product of claim 1 wherein each alcohol is unsubstituted.

3. The reaction product of claim 2 wherein the individual mole ratios of the hydroxy ether, the long chain alcohol and the short chain alcohol to $P_2O_5$ are within the ranges of 0.8:1 to 1.8:1; 0:1 to 1.4:1; and 0.9:1 to 2.0:1 respectively.

4. The reaction product of claim 3 wherein the total mole ratio of the hydroxy ether, the long chain alcohol and the short chain alcohol to total $P_2O_5$ ranges from about 2.8:1 to about 7.0:1.

5. The reaction product of claim 1 wherein the pentavalent phosphorus compound is $P_2O_5$.

6. The reaction product of claim 1 wherein the long chain monohydric alcohol contains from 5 to about 12 carbon atoms.

7. The reaction product of claim 6 wherein the short chain alcohol is a primary, unsubstituted, straight chain, saturated alcohol.

8. The reaction product of claim 7 wherein the short chain alcohol is ethanol, methanol, or a mixture thereof, and the long chain alcohol is unsubstituted.

9. The reaction product of claim 8 wherein the short chain alcohol is methanol.

10. The reaction product of claim 1 wherein the total mole ratio of the hydroxy ether, the long chain alcohol and the short chain alcohol to total $P_2O_5$ is about 3.64 to 1.

11. The reaction product of claim 1 wherein the reaction temperature ranges from about 80° to about 90° C. and the reaction time ranges from about 1.5 to about 3 hours.

12. The reaction product of claim 1 werein when the total carbon atoms of R and $R_1$ is 3 or 4 there is also reacted a short chain substantially unsubstituted monohydric aliphatic alcohol containing from 1 to 4 carbon atoms or a mixture of said alcohols.

13. The reaction product of claim 12 wherein the long chain alcohol is unsubstituted and contains from 5 to 12 carbon atoms, and wherein the short chain alcohol is methanol, ethanol, or a mixture thereof.

14. An organic phosphate ester composition prepared by the process which comprises the reaction of:
   A. a pentavalent phosphorus compound, selected from the group consisting of $P_2O_5$ and a mixture of $P_2O_5$ with polyphosphoric acid;
   B. a hydroxy ether of the formula $ROR_1OH$ wherein R is a $C_1$ to $C_6$ alkyl group, $R_1$ is a $C_2$ or $C_3$ alkylene group and the total carbon atoms of R and $R_1$ range from 3 to about 8; and
   C. when the total carbon atoms of R and $R_1$ is 3 or 4 a long chain substantially unsubstituted monohydric aliphatic alcohol containing at least 5 carbon atoms and a short chain substantially unsubstituted monohydric aliphatic alcohol containing from one to four carbon atoms; when the total carbon atoms of R and $R_1$ is five to eight a short chain substantially unsubstituted monohydric aliphatic alcohol containing from one to four carbon atoms;
the individual mole ratios of the hydroxy ether, the long chain alcohol and the short chain alcohol to total $P_2O_5$ being within the ranges of 0.4:1 to 4.5:1; 0:1 to 4.0:1 and 0:1 to 5:1 respectively, and the total mole ratio of said three components to total $P_2O_5$ being from about 2.8:1 to about 7.0:1,
said reaction being conducted by first reacting the phosphorus compound with the hydroxy ether, and when the total carbon atoms of R and $R_1$ is 3 or 4, also with the long chain alcohol for a period of time of from about 5 to about 30 minutes at a temperature of from about 70° to about 90° C., cooling the reaction mixture to below 70° C., adding the short chain alcohol to the reaction mixture and reacting the mixture at a temperature of from about 70° to about 90° C. for a period of time to provide a total reaction time of from about 1.5 to about 6 hours.

15. The reaction product of claim 14 wherein when the total carbon atoms of R and $R_1$ is five to eight there is also reacted with the pentavalent phosphorus compound and the hydroxy ether a long chain monohydric alcohol containing at least 5 carbon atoms prior to reacting the short chain alcohol.

16. The reaction product of claim 14 wherein the long chain alcohol has 5 to 12 carbon atoms.

17. The reaction product of claim 14 wherein the pentavalent phosphorus compound is $P_2O_5$.

18. The reaction product of claim 14 wherein the short chain alcohol is a primary, unsubstituted, straight chain, saturated alcohol.

19. The reaction product of claim 18 wherein the short chain alcohol is ethanol, methanol, or a mixture thereof, and the long chain alcohol is unsubstituted.

20. The reaction product of claim 19 wherein the short chain alcohol is methanol.

21. The reaction product of claim 19 wherein the short chain alcohol is ethanol.

22. The reaction product of claim 14 wherein each alcohol is unsubstituted.

23. The reaction product of claim 22 wherein the long chain alcohol has 5 to 12 carbon atoms; the pentavalent phosphorus compound is $P_2O_5$; and the short chain alcohol is primary, straight chain, and saturated.

24. The reaction product of claim 23 wherein said hydroxy ether is selected from the group consisting of ethylene glycol monomethyl ether, ethylene glycol monoethyl ether, ethylene glycol mono-n-butyl ether, ethylene glycol mono-n-hexyl ether, ethylene glycol monoisobutyl ether, propylene glycol monomethyl ether, propylene glycol monoisobutyl ether, propylene glycol monomethyl ether and mixtures thereof.

25. The reaction product of claim 24 wherein the individual mole ratios of the hydroxy ether, the long chain alcohol and the short chain alcohol to $P_2O_5$ are within the ranges of 0.8:1 to 1.8:1; 0:1 to 1.4:1; and 0.9:1 to 2.0:1 respectively.

26. The reaction product of claim 25 wherein the short chain alcohol is methanol, ethanol, or a mixture thereof.

27. The reaction product of claim 26 wherein the total mole ratio of the short chain alcohol, hydroxy ether and long chain alcohol to $P_2O_5$ is about 3.64:1.

28. The reaction product of claim 27 wherein the short chain alcohol is methanol.

29. A method of preparing an organic phosphate ester composition, said ester composition having as a property the ability to increase the viscosity of kerosene when admixed in kerosene with sodium aluminate, which comprises reacting:
   A. a pentavalent phosphorus compound selected from the group consisting of $P_2O_5$ and a mixture of $P_2O_5$ with polyphosphoric acid;
   B. a hydroxy ether of the formula $ROR_1OH$ wherein R is a $C_1$ to $C_6$ alkyl group, $R_1$ is a $C_2$ or $C_3$ alkylene group and the total carbon atoms of R and $R_1$ range from 3 to about 8; and
   C. when the total carbon atoms of R and $R_1$ is 3 or 4, a long chain substantially unsubstituted monohydric aliphatic alcohol containing at least 5 carbon atoms, but when the total carbon atoms of R and $R_1$ is 5 to 8, an alcohol selected from the group consisting of a long chain substantially unsubstituted monohydric aliphatic alcohol containing at least 5 carbon atoms, a short chain substantially unsubstituted monohydric aliphatic alcohol containing from 1 to 4 carbon atoms or a mixture of said alcohols, the individual mole ratios of the hydroxy ether, the long chain alcohol and the short chain alcohol to total $P_2O_5$ are within the ranges of 0.4:1 to 4.5:1; 0:1 to 4.0:1 and 0:1 to 5.0:1 respectively, said reaction being conducted at temperature ranging from about 70° to about 90° C. for a period of time of from about 1.5 to about 6 hours, and said pentavalent phosphorus compound, hydroxy ether, and alcohol or alcohols being provided in molar ratios and admixed in a sequence effective to provide a reaction product suitable for use in increasing the viscosity of kerosene.

30. The method of claim 29 wherein each alcohol is unsubstituted.

31. The method of claim 30 wherein the individual mole ratios of the hydroxy ether, the long chain alcohol and the short chain alcohol to $P_2O_5$ are within the ranges of 0.8:1 to 1.8:1; 0:1 to 1.4:1; and 0.9:1 to 2.0:1 respectively.

32. The method of claim 31 wherein the total mole ratio of the hydroxy ether, the long chain alcohol and the short chain alcohol to total $P_2O_5$ ranges from about 2.8:1 to about 7.0:1.

33. The method of claim 29 wherein the pentavalent phosphorus compound is $P_2O_5$.

34. The method of claim 29 wherein the long chain monohydric alcohol contains from 5 to about 12 carbon atoms.

35. The method of claim 34 wherein the short chain alcohol is a primary, unsubstituted, straight chain, saturated alcohol.

36. The method of claim 35 wherein the short chain alcohol is ethanol, methanol, or a mixture thereof, and the long chain alcohol is unsubstituted.

37. The method of claim 36 wherein the short chain alcohol is methanol.

38. The method of claim 29 wherein the total mole ratio of the hydroxy ether, the long chain alcohol and the short chain alcohol to total $P_2O_5$ is about 3.64 to 1.

39. The method of claim 29 wherein the reaction temperature ranges from about 80° to about 90° C. and the reaction time ranges from about 1.5 to about 3 hours.

40. The method of claim 29 wherein when the total carbon atoms of R and $R_1$ is 3 or 4 there is also reacted a short chain substantially unsubstituted monohydric aliphatic alcohol containing from 1 to 4 carbon atoms or a mixture of said alcohols.

41. The method of claim 40 wherein the long chain alcohol is unsubstituted and contains from 5 to 12 carbon atoms, and wherein the short chain alcohol is methanol, ethanol, or a mixture thereof.

42. A method of preparing an organic phosphate ester composition comprising reacting:
A. a pentavalent phosphorus compound, selected from the group consisting of $P_2O_5$ and a mixture of $P_2O_5$ with polyphosphoric acid;
B. a hydroxy ether of the formula $ROR_1OH$ wherein R is a $C_1$ to $C_6$ alkyl group, $R_1$ is a $C_2$ or $C_3$ alkylene group and the total carbon atoms of R and $R_1$ range from 3 to about 8; and
C. when the total carbon atoms of R and $R_1$ is 3 or 4 a long chain substantially unsubstituted monohydric aliphatic alcohol containing at least 5 carbon atoms and a short chain substantially unsubstituted monohydric aliphatic alcohol containing from one to four carbon atoms; when the total carbon atoms of R and $R_1$ is five to eight a short chain substantially unsubstituted monohydric aliphatic alcohol containing from one to four carbon atoms;
the individual mole ratios of the hydroxy ether, the long chain alcohol and the short chain alcohol to total $P_2O_5$ being within the ranges of 0.4:1 to 4.5:1; 0:1 to 4.0:1 and 0:1 to 5:1 respectively, and the total mole ratio of said three components to total $P_2O_5$ being from about 2.8:1 to about 7.0:1,
said reaction being conducted by first reacting the phosphorus compound with the hydroxy ether, and when the total carbon atoms of R and $R_1$ is 3 or 4, also with the long chain alcohol for a period of time of from about 5 to about 30 minutes at a temperature of from about 70° to about 90° C., cooling the reaction mixture to below 70° C., adding the short chain alcohol to the reaction mixture and reacting the mixture at a temperature of from about 70° to about 90° C. for a period of time to provide a total reaction time of from about 1.5 to about 6 hours.

43. The method of claim 42 wherein when the total carbon atoms of R and $R_1$ is five to eight there is also reacted with the pentavalent phosphorus compound and the hydroxy ether a long chain monohydric alcohol containing at least 5 carbon atoms prior to reacting the short chain alcohol.

44. The method of claim 42 wherein the long chain alcohol has 5 to 12 carbon atoms.

45. The method of claim 42 wherein the pentavalent phosphorus compound is $P_2O_5$.

46. The method of claim 42 wherein the short chain alcohol is a primary, unsubstituted, straight chain, saturated alcohol.

47. The method of claim 46 wherein the short chain alcohol is ethanol, methanol, or a mixture thereof, and the long chain alcohol is unsubstituted.

48. The method of claim 47 wherein the short chain alcohol is methanol.

49. The method of claim 47 wherein the short chain alcohol is ethanol.

50. The method of claim 42 wherein each alcohol is unsubstituted.

51. The method of claim 50 wherein the long chain alcohol has 5 to 12 carbon atoms; the pentavalent phosphorus compound is $P_2O_5$; and the short chain alcohol is primary, straight chain, and saturated.

52. The method of claim 51 wherein said hydroxy ether is selected from the group consisting of ethylene glycol monomethyl ether, ethylene glycol monoethyl ether, ethylene glycol mono-n-butyl ether, ethylene glycol mono-n-hexyl ether, ethylene glycol monoisobutyl ether, propylene glycol monomethyl ether, propylene glycol monoisobutyl ether, propylene glycol monomethyl ether and mixtures thereof.

53. The method of claim 52 wherein the individual mole ratios of the hydroxy ether, the long chain alcohol and the short chain alcohol to $P_2O_5$ are within the ranges of 0.8:1 to 1.8:1; 0:1 to 1.4:1; and 0.9:1 to 2.0:1 respectively.

54. The method of claim 53 wherein the short chain alcohol is methanol, ethanol, or a mixture thereof.

55. The method of claim 54 wherein the total mole ratio of the short chain alcohol, hydroxy ether and long chain alcohol to $P_2O_5$ is about 3.64:1.

56. The method of claim 55 wherein the short chain alcohol is methanol.

* * * * *

UNITED STATES PATENT AND TRADEMARK OFFICE
CERTIFICATE OF CORRECTION

PATENT NO. : 4,153,649
DATED : May 8, 1979
INVENTOR(S) : Thomas J. Griffin, Jr.

It is certified that error appears in the above-identified patent and that said Letters Patent are hereby corrected as shown below:

Col. 1, line 18, delete "Repesentative" and insert --Representative--.

Col. 2, line 56, delete "pimary" and insert --primary--.

Col. 8, Table I, last heading, after "(cps at 160 sec)" insert -- $^{-1}$ --.

Col. 10, Table I-continued, last heading, after "(cps at 160 sec)" insert -- $^{-1}$ --.

Col. 9, Table I-continued, Test No. 62, under heading " OH
                                                        $R_1$OR",
delete "Eb(1.5)" and insert --EB(1.5)--.

Col. 12, line 14, delete "and", second occurrence.

Signed and Sealed this

Thirtieth Day of October 1979

[SEAL]

Attest:

RUTH C. MASON
Attesting Officer

LUTRELLE F. PARKER
Acting Commissioner of Patents and Trademarks